United States Patent [19]

Klearman et al.

[11] Patent Number: 5,376,072
[45] Date of Patent: Dec. 27, 1994

[54] APPARATUS FOR AND METHOD OF, CRUSHING A PILL AND ADMINISTERING THE PILL INGREDIENTS

[75] Inventors: Jeffrey D. Klearman; Jeffrey J. Bierman; Eli Schachet, all of St. Louis, Mo.

[73] Assignee: Lake Medical Products, Inc., St. Louis, Mo.

[21] Appl. No.: 168,019

[22] Filed: Dec. 15, 1993

[51] Int. Cl.⁵ .............................................. A61M 37/00
[52] U.S. Cl. .................................. 604/82; 604/218; 604/92; 604/56
[58] Field of Search .................. 604/56, 82, 83, 92, 604/187, 191, 211, 222, 218, 224, 225, 57, 77–79, 84–85

[56] References Cited

U.S. PATENT DOCUMENTS

| | | | |
|---|---|---|---|
| 1,165,686 | 12/1915 | McElroy | 604/222 |
| 4,057,052 | 11/1977 | Kaufman et al. | 604/222 |
| 4,568,331 | 2/1986 | Fischer et al. | 604/56 |
| 4,715,854 | 12/1987 | Vaillancourt | 604/191 |
| 4,765,549 | 8/1988 | Sherman | 241/169 |
| 5,118,021 | 6/1992 | Flocchi | 225/103 |

OTHER PUBLICATIONS

American Medical Industries brochure entitled "Making Your Medications & Vitamnins EZ to Swallow", including enclosure entitled Remembering Your Medication Schedule is EZ.

American Medical Industries sales flier entitled "Welcome to American Medical Industries" Family of EZ-Health TM Products, 1993.

American Medical Industries Facsimile transmission to Lake Medical Products regarding EZ-Swallow Pill Crushers & Pill Splitters, Sep. 1, 1993.

*Primary Examiner*—C. Fred Rosenbaum
*Assistant Examiner*—Perry E. Van Over
*Attorney, Agent, or Firm*—Rogers, Howell & Haferkamp

[57] ABSTRACT

A pill crushing syringe includes a barrel and a plunger, with abraded surfaces on each so that a pill placed in the barrel is crushed as the plunger advances within the barrel. The barrel has an aperture located near the closed end with a catheter connected around and extending from the aperture. The plunger has a sealing gland to provide an airtight seal with the barrel so that liquid may be drawn into the barrel through the aperture by withdrawing the plunger from the barrel to thereby suspend the crushed pill in the liquid, and the suspension may be flushed from the barrel by thereafter advancing the plunger into the barrel.

23 Claims, 2 Drawing Sheets

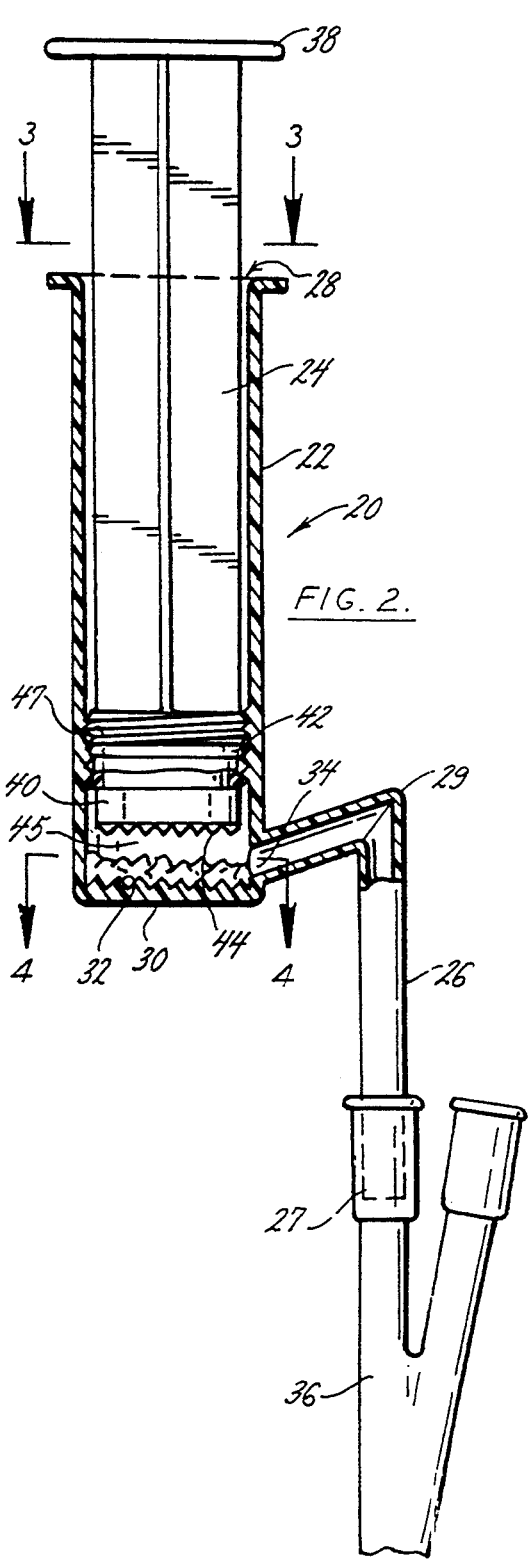
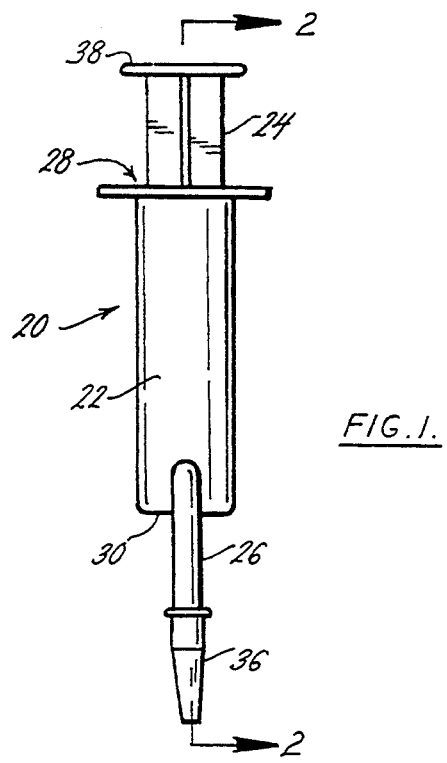
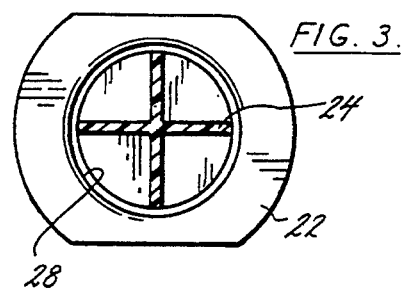
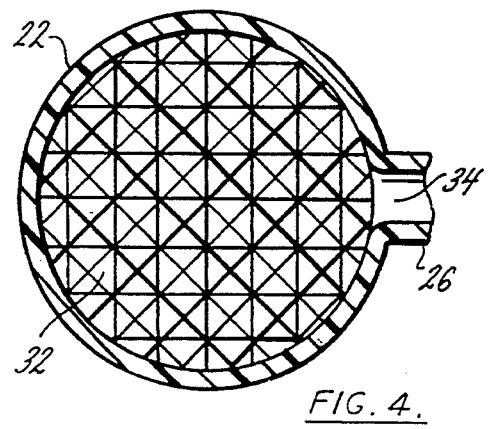
FIG. 1.
FIG. 2.
FIG. 3.
FIG. 4.

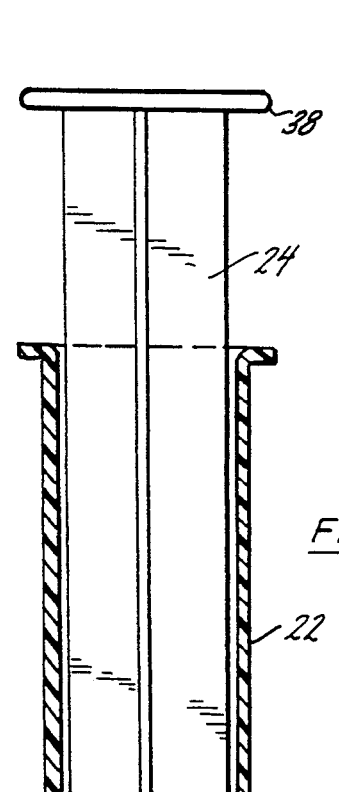
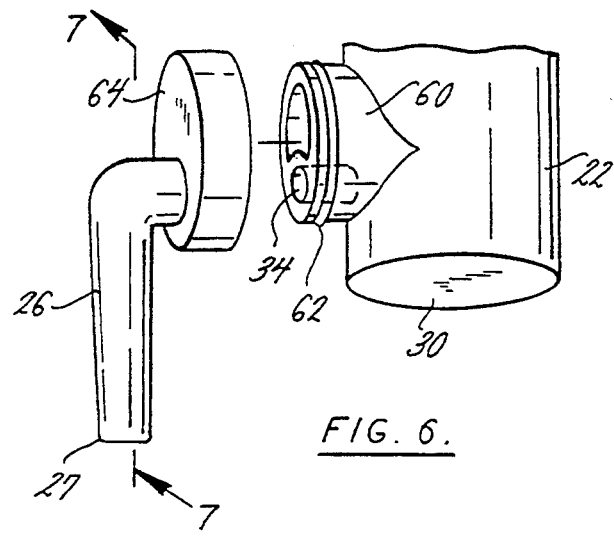
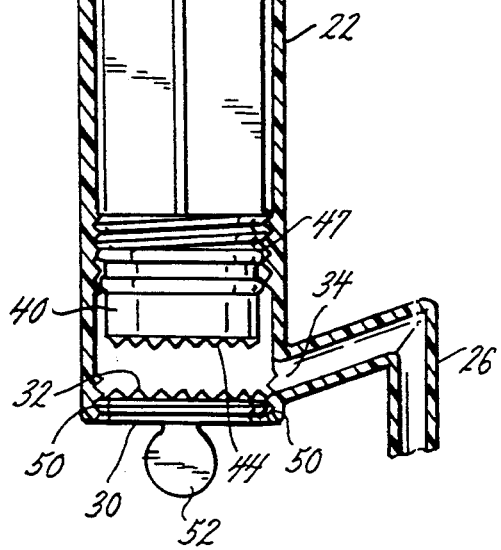
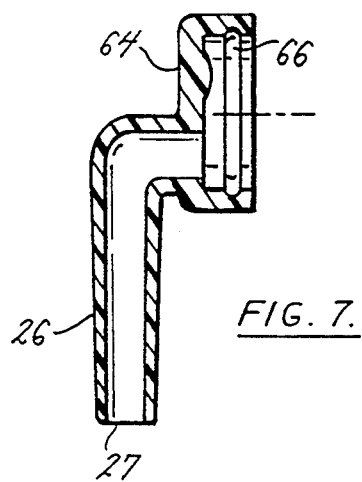
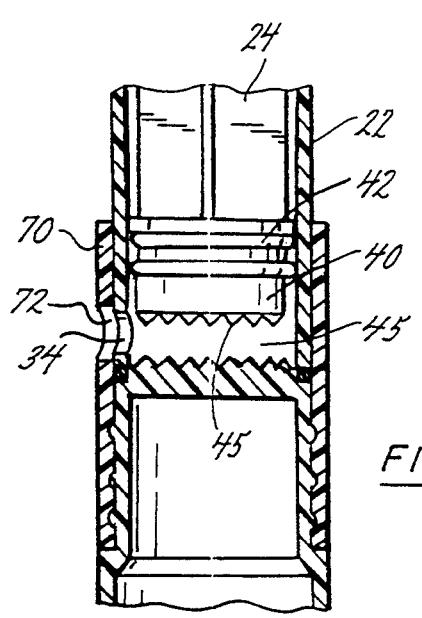
FIG. 5.
FIG. 6.
FIG. 7.
FIG. 8.

5,376,072

APPARATUS FOR AND METHOD OF, CRUSHING A PILL AND ADMINISTERING THE PILL INGREDIENTS

FIELD OF THE INVENTION

This invention relates to an apparatus for, and method of, crushing a pill, mixing the resulting powder with a liquid and administering the suspension.

BACKGROUND AND SUMMARY OF THE INVENTION

In many instances, it is difficult if not impossible to administer medication in capsule form to patients. This is particularly true for patients who may be comatose or otherwise physically unable to swallow the pills. For those people, in the prior art, the pills were ground with a mortar and pestle. The powder was transferred to a liquid-filled container and mixed with the liquid. The suspension was then either swallowed, or a syringe was filled with the suspension and injected into an intravenous tube or other tube generally used in hospital settings.

The prior art technique carried several drawbacks. The most serious of these were the risks of low and unpredictable compliance and cross-contamination. As the pill was crushed in a mortar and then transferred to another container before being administered, a nurse using extreme care could not help but lose some of the pill as residue on the mortar, pestle, etc. Furthermore, this residue would necessarily vary both in quantity and content from dose to dose to thereby perhaps alter the dosage administered from that intended. In extreme situations, this could interfere with achieving the desired medical result.

The undesired, but inescapable, residue also created an unavoidable risk of cross-contamination as the same mortar and pestle were typically re-used for the same and other patients, as well.

Moreover, the prior art technique was very time consuming as the nurse needed to use care and caution to avoid spillage, which translated into increased nurse or medical technician time and expense.

Other pill crushing devices are also known in the prior art. However, similar to the mortar and pestle technique discussed above, these devices were designed to grind or crush the pill in one compartment, transfer the powder to another liquid-filled container where the powder was dissolved or suspended and then administered. These devices similarly carried the risks of contamination, cross-contamination, spillage and waste, and were again time consuming.

The present invention overcomes the foregoing problems by providing a pill crushing syringe which is adapted to crush medication, preferably a pill, and mix the resulting powder with liquid all within the syringe itself, and then administer the suspension with the same syringe. Generally the syringe of the present invention includes a barrel and a plunger. The syringe has two opposing abraded surfaces, one on the plunger and one in the barrel bottom, to crush a pill placed in the barrel by the plunger as it is advanced to the bottom of the barrel. The pill could even be "ground" by rotating the plunger within the barrel to achieve a complete breakdown of the pill into small and regularly sized particles. In an alternate embodiment, the bottom of the barrel may be threaded so that it may also be rotated, thereby permitting both abraded surfaces to be positively driven with respect to each other. The barrel includes an aperture and a catheter located at the bottom of the barrel for drawing liquid into the barrel to mix with the crushed pill particles. The plunger includes a sealing gland providing an airtight relationship between the plunger and the barrel to assist in drawing liquid into the barrel by withdrawing the plunger from the barrel when the catheter tip is submerged in the liquid. The suspension of the liquid and crushed pill particles is administered by advancing the plunger into the barrel thereby forcing the suspension through the catheter and into a tube attached to the patient.

Generally, the method of this invention comprises providing a pill crushing syringe including a barrel and a plunger with opposing abraded surfaces so that medication, preferably a pill, placed in the barrel is crushed as the plunger is "bottomed" within the barrel, placing a pill into the barrel, crushing the pill, adding liquid to the barrel thereby suspending the powder in the liquid, and flushing the suspension.

The apparatus and method of this invention are significant improvements over the prior art in that pills are crushed, the resulting powder mixed with liquid, and the suspension administered all with the same syringe. Because the pill is crushed in a closed container and the powder need not be transferred for mixing with the liquid, the risk of cross-contamination and spillage is greatly reduced while consistency of compliance is achieved. Moreover, in the present invention, the abraded surfaces used to crush the pills are exposed to the liquid drawn into the barrel which provides a "washing" action on the very surfaces used to grind the pill. This helps to minimize residue.

In addition to reducing the risk of waste and contamination, insuring a high dosage compliance rate, and eliminating the problem of cleaning the pestle and mortar, the present invention saves nurses time allowing more medicinal dosages to be administered within the same time frame in a reliable manner. Further, the syringe may be made of plastic and used only once, thereby eliminating the risk of cross-contamination

BRIEF DESCRIPTION OF THE DRAWINGS

In the accompanying drawings which form a part of the specification and are to be read in conjunction therewith, and in which like reference numerals are used to indicate like parts in the various views:

FIG. 1 is an elevation view of the pill crushing syringe constructed according to the principles of this invention;

FIG. 2 is a cross-sectional view taken along lines 2—2 in FIG. 1 detailing the interior construction of the syringe;

FIG. 3 is a cross-sectional view taken along lines 3—3 in FIG. 2 detailing the construction of the plunger;

FIG. 4 is a cross-sectional view taken along lines 4—4 in FIG. 2 detailing the construction of the abraded surface;

FIG. 5 is a cross-sectional view of the closed bottom constructed according to an alternative embodiment of this invention permitting the bottom to be rotated relative to the syringe barrel and plunger:

FIG. 6 is an exploded isometric view of a second alternative embodiment of the invention illustrating the catheter and cap from the stub housing;

FIG. 7 is a cross-sectional view taken along lines 7—7 in FIG. 6 detailing the catheter position relative to the cap and the groove within the cap; and FIG. 8 is a cross-sectional view of a third alternative embodiment of the invention illustrating the collar and collar aperture of the adjustable sealing means.

DETAILED DESCRIPTION OF THE PREFERRED EMBODIMENT

A pill crushing syringe constructed according to the principles of this invention is indicated generally as 20 in FIG. 1. The syringe includes a barrel 22, a plunger 24, and a catheter 26.

The barrel 22 includes an open end 28 and a preferably flat closed end 30. The closed end 30 has an interior abraded surface 32 which is shown in FIGS. 2 and 4 as preferably serrated. An aperture 34 is formed through the barrel wall preferably adjacent to the abraded surface 32, and the catheter 26 is connected around and extends from aperture 34. The catheter 26 is shown in FIG. 2 as preferably having a crook 29 and including a tip 27 for insertion into a tube 36. In the preferred embodiment, the tube 36 is an intravenous tube, such as a nasal-gastric tube, gastrostomy tube or a jejunostomy tube, for example.

The plunger 24 includes a handle end 38, a tip end 40, and a sealing gland 42 providing an airtight relationship between the plunger and the barrel. An abraded surface 44 is located on the tip end 40 positioned to engage the barrel abraded surface 32. In the preferred embodiment, the abraded surface 44 is serrated and the sealing gland 42 is preferably integral with the plunger abraded surface 44. A cavity or space 45 is defined within the barrel 22 between the abraded surfaces 32 and 44, and the aperture 34 creates a fluid connection between catheter 26 and cavity 45.

The plunger 24 is removable from the barrel 22 to allow medication, preferably a pill (not shown), to be placed in the barrel. The plunger is also adapted to rotate within the barrel to assist in grinding the pill between abraded surfaces 32 and 44. The barrel 22 and the plunger 24 may include a threaded fitting 47 which advances the plunger into the barrel as the plunger is rotated therein (see FIGS. 2 and 5). The threaded fitting creates a positive grinding action between the abraded surfaces 32 and 44 as the plunger is rotated within the barrel.

The seal created by sealing gland 42 allows liquid to be drawn into the barrel by withdrawing the plunger from the barrel as the catheter tip 27 is submerged in a container of water or the like. The barrel may then be flushed, and the suspension comprising the crushed pill and water evacuated from the syringe, by advancing the plunger into the barrel thereby forcing the suspension through the catheter.

In an alternative embodiment, the closed end 30 is screw thread fastened to the barrel 22 by threaded grooves 50 (see FIG. 5). The closed end 30 is thereby rotatable with respect to the rest of barrel 22 and is removable. The closed end 30 may comprise a thumb screw 52, for example. In this embodiment, the pill may be placed in the barrel 22 by removing the closed end 30 and the closed end may be rotated to facilitate crushing and grinding the pill.

According to a second alternative embodiment, the syringe 20 includes means for adjustably sealing the fluid connection between catheter 26 and cavity 45. The adjustable sealing means allows liquid to be temporarily trapped within the cavity. One example of the adjustable sealing means is illustrated in FIG. 6. The barrel 22 further includes a stub housing 60 extending radially, and non-concentrically, from aperture 34, and a retaining lip 62 extends around the outside surface of the stub housing. The aperture 34 extends through the stub housing 60.

Catheter 26 includes a cap 64 rotatably coupled to the stub housing and extending radially, and non-concentrically, from the catheter end opposite tip 27. The cap 64 includes a groove 66 (see FIG. 7) appropriately sized to mate with retaining lip 62 thereby creating a liquid-tight seal between the cap and grub housing. The cap 64, being rotatable about the stub housing axis, may be rotated to align the catheter and the aperture for fluid connection, or to mis-align the catheter and aperture to seal the connection.

Another example of the adjustable sealing means is illustrated in FIG. 8. A collar 70, having a collar aperture 72, is fitted around the barrel 22 in a substantially fluid tight relationship. The collar 70 is rotatable about the barrel axis and may alternately be rotated to align the collar aperture 72 with the barrel aperture 34, creating a fluid connection therebetween, or to seal the apertures 34 and 72 from each other.

According to the method of this invention, the plunger 24 is removed from the barrel 22 and medication, preferably a pill (not shown), is placed in the barrel. The plunger is advanced into the barrel until the pill is lodged snugly between the abraded surfaces 32 and 44. The plunger 24 is then rotated as pressure is exerted thereon and against the pill thereby rotating abraded surface 44 with respect to abraded surfaces 32 until the pill is crushed and/or ground into a powder 48. The tip 27 of catheter 26 is placed in a liquid, a glass of water for example, and the plunger 24 is withdrawn from the barrel thereby drawing liquid into the barrel cavity 45 to mix with the powder 48 of the crushed pill. The catheter 27 has a crook 29 formed therein to inhibit the free flow of liquid out of the catheter after it is withdrawn from the glass. This helps prevent any of the suspended pill particles from escaping. The syringe 20 may then be shaken to dislodge any powder residue off the abraded surfaces 32 and 44. During shaking, it may be desirable to close off the end of tip 27 to prevent any of the suspension from escaping. The tip 27 of catheter 26 is then inserted into tube 36 and the suspension within the barrel is flushed from the syringe by advancing the plunger into the barrel.

According to an alternative embodiment of this method the pill may be placed into the barrel 24 by unscrewing and removing the closed end 30 (see FIG. 5), placing the pill into the barrel, and replacing the closed end. The plunger is then advanced into the barrel until the pill is squeezed snugly between abraded surfaces 32 and 44. The pill may be crushed and/or ground by twisting the closed end 30 within the threaded grooves 50 to thereby rotate abraded surface 32 with respect to abraded surface 44. Further, the barrel 22 can be held steady while simultaneously rotating the plunger within the barrel and twisting the closed end 30 within the threaded grooves 50. This technique provides relative motion between both of the abraded surfaces and the barrel, thereby intensifying the grinding action.

According to a second alternative embodiment of this method, once the liquid is drawn into cavity 45 to mix with powder 48, the fluid connection between the catheter 26 and the cavity 45 is temporarily sealed. This allows the syringe to be shaken, violently if necessary, without the possibility of losing liquid or medication from the syringe. Once the powder is fully suspended in the liquid, the catheter-cavity fluid seal is restored and the suspension is flushed from the syringe by advancing the plunger into the barrel.

While the medication placed in the barrel 22 is preferably a pill, the term "pill" is intended to include tablets, capsules, and other discrete units of medication. The pill may also include particles, powder, or liquid forms of medication. For instance, a capsule may be provided which houses medication within a shell. The medication may be placed in the barrel by holding the capsule over the open end 28 of the barrel and breaking the capsule shell thereby dropping the medication into the barrel. If the form of medication is not readily suspended in water, the syringe 20 crushes and/or grinds the medication as disclosed above.

It is understood that the above-described pill crushing method may be practiced without administering the dosage through the catheter into an intravenous tubing. Alternatively, the suspension may be delivered to a tissue site, for example, or elsewhere as needed or desired.

It is further understood that the syringe 20 may be intended for single use application, made of plastic or other suitable disposable material, and disposed of after one usage to eliminate cross-contamination. Further, the syringe may comprise an electric pill crusher with removable plastic inserts or surfaces for the plunger, barrel, and/or catheter, the removable plastic inserts being replaceable for single use application. In this variation, the plunger can be electrically advanced and rotated to crush the pill, withdrawn to mix the suspension, and even advanced a second time to administer.

Although illustrated embodiments of the present invention are described herein with reference to the accompanying drawings, it is to be understood that the invention is not limited to those precise embodiments and that various other changes and modifications may be effected therein by one skilled in the art without departing from the scope or spirit of the invention. The scope of the invention is defined solely by the claims, and their equivalents.

What is claimed is:

1. A pill crushing syringe comprising a barrel, having an aperture to facilitate drawing a liquid into the barrel and expelling the liquid therefrom a plunger moveable within said barrel, and each of the barrel and the plunger having included thereon at least one abraded surface so that a pill placed within said syringe and adjacent said abraded surfaces is crushed as said plunger is moved within the barrel.

2. The pill crushing syringe of claim 1 wherein the plunger abraded surface is positioned to engage the barrel abraded surface as the plunger is advanced therein.

3. The pill crushing syringe of claim 2 wherein the barrel further includes an open end and a closed end, the barrel abraded surface being located on the closed end, and wherein the plunger further includes a tip end, the plunger abraded surface being located on the tip end.

4. The pill crushing syringe of claim 3 wherein the barrel permits the rotation of the plunger therein to thereby facilitate the grinding of a pill between the abraded surfaces.

5. The pill crushing syringe of claim 4 wherein the plunger and the barrel include a threaded fitting, said threaded fitting advancing the plunger into the barrel as the plunger is rotated therein, thereby creating a positive grinding action between the abraded surfaces.

6. The pill crushing syringe of claim 4 further comprising a space between said abraded surfaces, the aperture communicating with said space, a catheter, and a fluid connection between said catheter and said aperture so that liquid may be drawn through the catheter and into said space by withdrawing said plunger from within said barrel as said catheter is submerged in a liquid.

7. The pill crushing syringe of claim 6 further comprising means for adjustably sealing said fluid connection so that the liquid may be temporarily trapped in said space.

8. The pill crushing syringe of claim 7 wherein the adjustable sealing means further comprises a non-concentrical cap rotatably mounted to the barrel.

9. The pill crushing syringe of claim 6 further comprising a sealing gland between said plunger and said barrel to thereby provide a substantially airtight seal therebetween.

10. The pill crushing syringe of claim 9 wherein said catheter has a crook formed therein to thereby inhibit said liquid from flowing out of said catheter after being withdrawn from said liquid.

11. The pill crushing syringe of claim 3 wherein said barrel closed end is secured to said barrel by a threaded fitting, said threaded fitting permitting said closed end to be rotated with respect to said barrel and thereby grind said pill between said abraded surfaces.

12. A pill crushing syringe comprising:
a barrel, a plunger moveable within the barrel, each of the barrel and the plunger having included thereon one of a pair of opposing abraded surfaces so that as the plunger is advanced within the barrel the abraded surfaces squeeze a pill placed in the barrel to thereby crush it;
the barrel further including a space between said pair of opposing abraded surfaces and an aperture in the barrel communicating with the space; and
the plunger further including a sealing gland providing an airtight relationship between the plunger and the barrel so that a liquid may be drawn into the space between the abraded surfaces through the aperture by withdrawing the plunger from the barrel to thereby suspend the crushed pill in the liquid.

13. The pill crushing syringe of claim 12 wherein the barrel further includes an open end and a closed end, the barrel abraded surface being located on the closed end, and wherein the plunger further includes a tip end, the plunger abraded surface being located on the tip end.

14. The pill crushing syringe of claim 13 further including a catheter connected around the aperture and a fluid connection between the catheter and the aperture, to facilitate drawing the liquid into the barrel.

15. The pill crushing syringe of claim 14 further comprising means for adjustably sealing said fluid connection so that the liquid may be temporarily trapped in the space.

16. The pill crushing syringe of claim 15 wherein the barrel permits the rotation of the plunger therein to thereby facilitate grinding of the pill between the abraded surfaces.

17. The pill crushing syringe of claim 16 wherein the plunger and the barrel include a threaded fitting, said threaded fitting advancing the plunger into the barrel as the plunger is rotated therein, thereby creating a positive grinding action between the abraded surfaces.

18. The pill crushing syringe of claim 17 wherein the barrel closed end is secured to the barrel by a threaded fitting, the threaded fitting permitting the closed end to be rotated with respect to the barrel and thereby grind the pill between the abraded surfaces.

19. The pill crushing syringe of claim 16 wherein the sealing gland is integral with the plunger abraded surface.

20. A method of administering a pill dosage through a tube into a patient, the method including the steps of:
providing a pill crushing syringe including a barrel having an open end, a closed end, an aperture, and a catheter connected around and extending from the aperture, a plunger having a tip end, and a tube in communication with the barrel wherein the barrel has an abraded surface located at an end and the plunger has an abraded surface located on the tip end such that the plunger abraded surface is positioned to engage the barrel abraded surface as the plunger is advanced in the barrel;
placing the pill into the barrel;
crushing the pill by advancing the plunger into the barrel to thereby bring the abraded surfaces into contact with the pill;
rotating the plunger within the barrel to thereby grind the pill into a powder between the abraded surfaces;
submerging the catheter into a liquid and drawing the liquid into the barrel by withdrawing the plunger from within the barrel to thereby suspend the powder in the liquid;
connecting the catheter to the tube; and
flushing the suspension out of the barrel and through the tube by advancing the plunger within the barrel, 21. The method of claim 20 wherein the pill comprises a capsule which houses medication within a shell, the step of placing the pill into the barrel further includes the step of positioning the capsule over the barrel and breaking the capsule shell thereby dropping the medication into the barrel, and the step of crushing the pill further includes the step of crushing the medication, 22. In a syringe, the syringe having a barrel and a plunger slidably received in the barrel, the improvement comprising a pair of opposing abraded surfaces, one on each of the barrel and the plunger so that a pill placed in the barrel and adjacent the abraded surfaces is squeezed by the abraded surfaces and crushed as the plunger is moved within the barrel.

23. The syringe of claim 22 wherein the barrel further includes an aperture in the barrel communicating with a space between the pair of abraded surfaces and a catheter connected around the aperture, the plunger further including a sealing gland providing an airtight relationship between the plunger and the barrel so that a liquid may be drawn through the catheter and the aperture into the space between the abraded surfaces by withdrawing the plunger from the barrel to thereby suspend the crushed pill in the liquid.

* * * * *